(12) United States Patent
Lu et al.

(10) Patent No.: US 11,262,863 B2
(45) Date of Patent: Mar. 1, 2022

(54) SENSING COMPONENT AND PULSE MEASURING METHOD

(71) Applicant: AU Optronics Corporation, Hsin-Chu (TW)

(72) Inventors: Wen-Je Lu, Hsin-Chu (TW); Yu-Jung Liu, Hsin-Chu (TW)

(73) Assignee: AU OPTRONICS CORPORATION, Hsin-Chu (TW)

( * ) Notice: Subject to any disclaimer, the term of this patent is extended or adjusted under 35 U.S.C. 154(b) by 466 days.

(21) Appl. No.: 16/513,870

(22) Filed: Jul. 17, 2019

(65) Prior Publication Data
US 2020/0073505 A1 Mar. 5, 2020

(30) Foreign Application Priority Data

Aug. 29, 2018 (TW) .................................. 107130167
Jan. 17, 2019 (TW) .................................. 108101871

(51) Int. Cl.
*G06F 3/041* (2006.01)
*G06F 3/043* (2006.01)
*H01L 41/113* (2006.01)

(52) U.S. Cl.
CPC .......... *G06F 3/0414* (2013.01); *G06F 3/0436* (2013.01); *H01L 41/1132* (2013.01); *G06F 2203/04105* (2013.01); *G06F 2203/04106* (2013.01)

(58) Field of Classification Search
CPC ................. G06F 3/0414; G06F 3/0436; G06F 2203/04105; G06F 2203/04106; H01L 41/1132; A61B 2562/0247; A61B 5/02444
See application file for complete search history.

(56) References Cited

U.S. PATENT DOCUMENTS

2010/0052880 A1 3/2010 Laitinen et al.
2014/0081160 A1* 3/2014 Xiang .................. A61B 5/0245
600/500

(Continued)

FOREIGN PATENT DOCUMENTS

CN 102579013 A 7/2012
CN 202568218 U 12/2012

(Continued)

*Primary Examiner* — Amit Chatly
(74) *Attorney, Agent, or Firm* — WPAT, PC

(57) ABSTRACT

A sensing component includes multiple piezoelectric pressure sensors. The piezoelectric pressure sensor includes a piezoelectric material layer, a thin film transistor array and an induced electrode. The piezoelectric material layer is configured to measure pulse at multiple positions to generate the corresponding multiple pulse signals. The thin film transistor array electrically coupled to the piezoelectric material layer includes multiple transistors. The transistor includes a first terminal, a second terminal and a control terminal. The first terminal is configured to receive one of the pulse signals. The second terminal coupled to a data line is configured to output a first sensing signal according to the one of the pulse signals. The control terminal is configured to receive a clock signal. The induced electrode coupled to the piezoelectric material layer is configured to receive another one of the pulse signals to output a second sensing signal.

8 Claims, 10 Drawing Sheets

(56) References Cited

U.S. PATENT DOCUMENTS

| | | | |
|---|---|---|---|
| 2014/0354905 A1* | 12/2014 | Kitchens | G01S 7/52085 349/12 |
| 2015/0016223 A1* | 1/2015 | Dickinson | G06F 3/0436 367/87 |
| 2015/0031964 A1* | 1/2015 | Bly | A61B 5/681 600/301 |
| 2015/0123931 A1 | 5/2015 | Kitchens et al. | |
| 2016/0071493 A1 | 3/2016 | Yoshiga | |
| 2019/0110758 A1* | 4/2019 | Kang | G16H 40/63 |
| 2020/0013946 A1* | 1/2020 | Cakmak | H01L 41/193 |

FOREIGN PATENT DOCUMENTS

| | | |
|---|---|---|
| CN | 104586370 A | 5/2015 |
| CN | 106419862 A | 2/2017 |
| TW | M550123 U | 10/2017 |

\* cited by examiner

SENSING COMPONENT AND PULSE MEASURING METHOD

RELATED APPLICATIONS

This application claims priority to Taiwan Application Serial Number 107130167, filed Aug. 29, 2018, and Taiwan Application Serial Number 108101871, filed Jan. 17, 2019, which is herein incorporated by reference.

BACKGROUND

Technical Field

The disclosure relates to a sensing component and a pulse measuring method, particularly to a sensing component with compensation and a pulse measuring thereof.

Description of Related Art

It is a common method used by Chinese medicine practitioners to obtain the pulse of the patient by pressing on the patient's wrist and to diagnosis the physiological and pathological condition of the human body according to the pulse.

Therefore, how to improve the pulse measuring method to improve the accuracy of the result is one of the important issues in this field.

SUMMARY

One aspect of the present disclosure is a sensing component including a piezoelectric pressure sensor. The piezoelectric pressure sensor includes a piezoelectric material layer, a thin film transistor array and an induced electrode. The piezoelectric material layer is configured to measure pulse at multiple positions to generate the corresponding multiple pulse signals. The thin film transistor array coupled to the piezoelectric material layer includes multiple transistors. The transistor includes a first terminal, a second terminal and a control terminal. The first terminal is configured to receive one of the pulse signals. The second terminal coupled to a data line is configured to output a first sensing signal according to the one of the pulse signals. The control terminal is configured to receive a clock signal. The induced electrode coupled to the piezoelectric material layer is configured to receive another one of the pulse signals to output a second sensing signal.

Another aspect of the present disclosure is a pulse measuring method including: measuring, by a piezoelectric material layer of a piezoelectric pressure sensor, pulses of multiple positions to generate a corresponding multiple pulse signals; receiving, by multiple transistors in a thin film transistor array in the piezoelectric pressure sensor, the corresponding the multiple pulse signals to output multiple first sensing signals; and receiving, by at least an induced electrode in the piezoelectric pressure sensor, one of the multiple pulse signals to output a second sensing signal.

DETAILED DESCRIPTION

The following embodiments are disclosed with accompanying diagrams for detailed description. For illustration clarity, many details of practice are explained in the following descriptions. However, it should be understood that these details of practice do not intend to limit the present disclosure. That is, these details of practice are not necessary in parts of embodiments of the present disclosure. Furthermore, for simplifying the diagrams, some of the conventional structures and elements are shown with schematic illustrations.

The terms used in this specification and claims, unless otherwise stated, generally have their ordinary meanings in the art, within the context of the disclosure, and in the specific context where each term is used.

It will be understood that, although the terms "first," "second," etc., may be used herein to describe various elements, these elements should not be limited by these terms. These terms are used to distinguish one element from another. For example, a first element could be termed a second element, and, similarly, a second element could be termed a first element, without departing from the scope of the embodiments.

In this document, the term "coupled" may also be termed "electrically coupled," and the term "connected" may be termed "electrically connected." "Coupled" and "connected" may also be used to indicate that two or more elements cooperate or interact with each other.

Figure 1A:
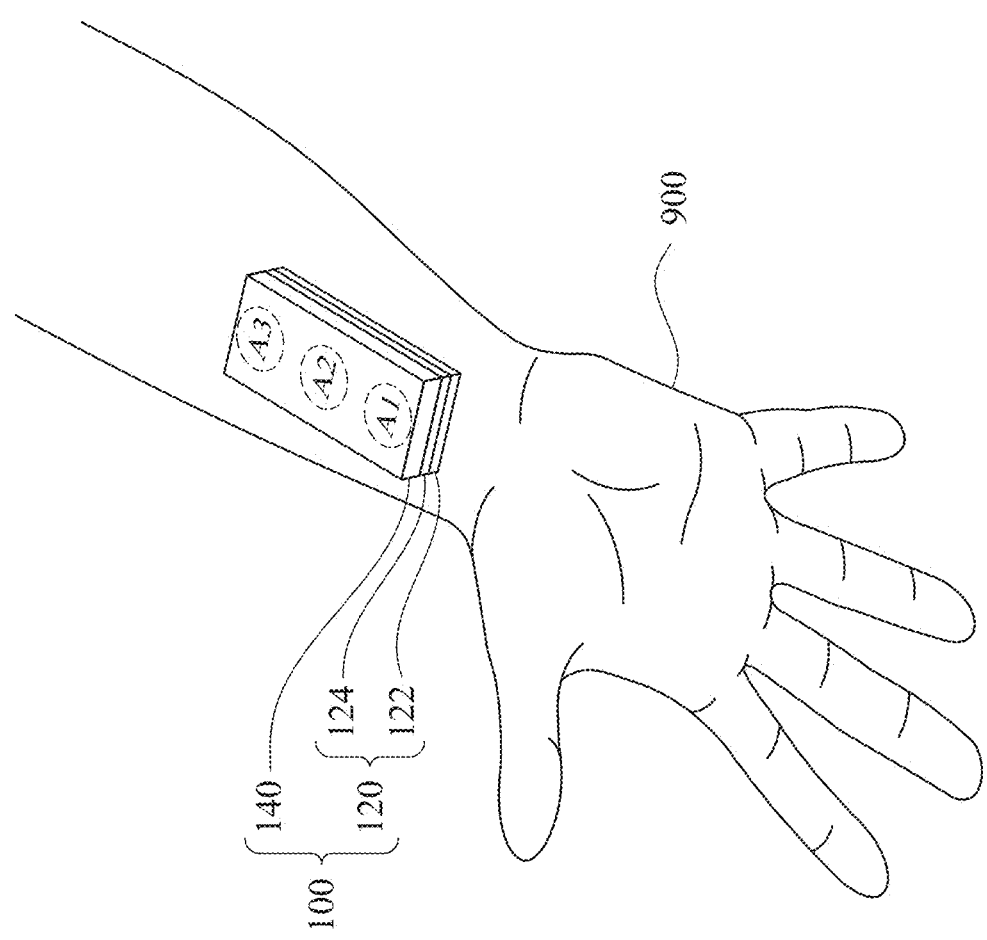
FIG. 1A and FIG. 1B are situational diagrams illustrating a sensing component in accordance with some embodiments of the disclosure.
Figure 1B:
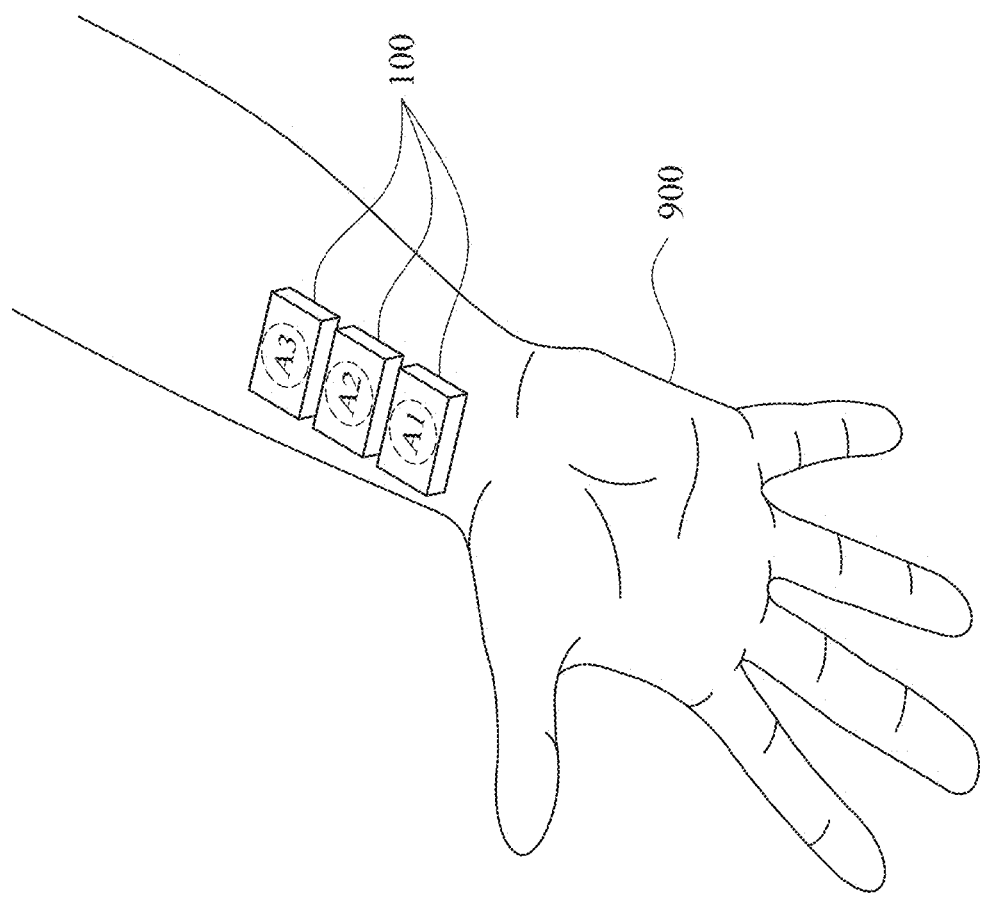

Please refer to FIG. 1A and FIG. 1B. FIG. 1A and FIG. 1B are situational diagrams illustrating a sensing component 100 in a pulse measuring apparatus in accordance with some embodiments of the disclosure. As shown in FIG. 1A and FIG. 1B respectively, when the pulse measuring apparatus of the present disclosure is operated, the one or more sensing components 100 in the pulse measuring apparatus are arranged on the wrist 900 to measure the pulse of the brachial artery in the wrist. For example, the sensing component 100 may be one, two or three.

In some embodiments, as shown in FIG. 1A, the sensing component 100 includes a piezoelectric pressure sensor 120 and a capacitive pressure sensor 140. The piezoelectric pressure sensor 120 includes a piezoelectric material layer 124 and a thin film transistor array 122. Configurationally, the capacitive pressure sensor 140 is coupled to the piezoelectric material layer 124 in the piezoelectric pressure sensor 120. The piezoelectric material layer 124 is coupled to the thin film transistor array 122. The thin film transistor array 122 is arranged on the wrist 900. In some embodiments, the piezoelectric material layer 124 may be realized by polyvinylidene difluoride (PVDF), but not intended to limit to it, in other embodiments, the piezoelectric material layer 124 may also be realized by polyvinyl fluoride (PVF), Polyvinylchloride (PVC), poly-γ-methyl-L-glutamate, and nylon-11 or other piezoelectric materials having the same properties.

Operationally, during measuring the pulse, three indenters (not shown in figure) of the pulse measuring apparatus are located above the areas A1, A2 and A3 in the FIG. 1A and FIG. 1B, respectively, and configured to apply a floating, medium or sinking force to the cubit position of the wrist 900 through the sensing component 100 of the pulse measuring apparatus, to apply a floating, medium or sinking force to the bar position of the wrist 900, and/or to apply a floating, medium or sinking force on the inch position of the wrist 900, so as to simulate the method used by the Chinese medicine practitioner to obtain the pulse. When the indenter of the pulse measuring apparatus applies stress to the positions of the area A1, A2 or A3, the capacitive pressure sensor 140 in the sensing component 100 of the pulse measuring apparatus is configured to measure the static pressure value at the corresponding position (cubit, bar or inch) and the corresponding force (floating, medium or sinking). And the piezoelectric pressure sensor 120 in the sensing component 100 of the pulse measuring apparatus is configured to measure the pulse at the corresponding position (cubit, bar or inch) and the corresponding force (floating, medium or sinking).

For example, when the indenter applies the force to the area A1 of the wrist 900 (i.e., the cubit position of the wrist 900), the capacitive pressure sensor 140 corresponds to the pressure of the area A1 to measure the force applied by the indenter. For another example, when the indenter applies forces with a first stress, a second stress and a third stress respectively to the area A1 of the wrist 900 (i.e., the cubit position of the wrist 900), the piezoelectric pressure sensor 120 measures the frequency and amplitude of the pulse of the floating, medium and sinking corresponding to the area A1 (i.e., the cubit position of the wrist 900) respectively.

It should be noted that, the number of the indenters, the size or the position of the areas A1~A3 above are merely examples, not intended to limit the present disclosure. Those of ordinary skills in the art without departing from the principle and spirit of the disclosure may set different numbers or adjust the size of the coverage areas based on actual needs.

Figure 2:
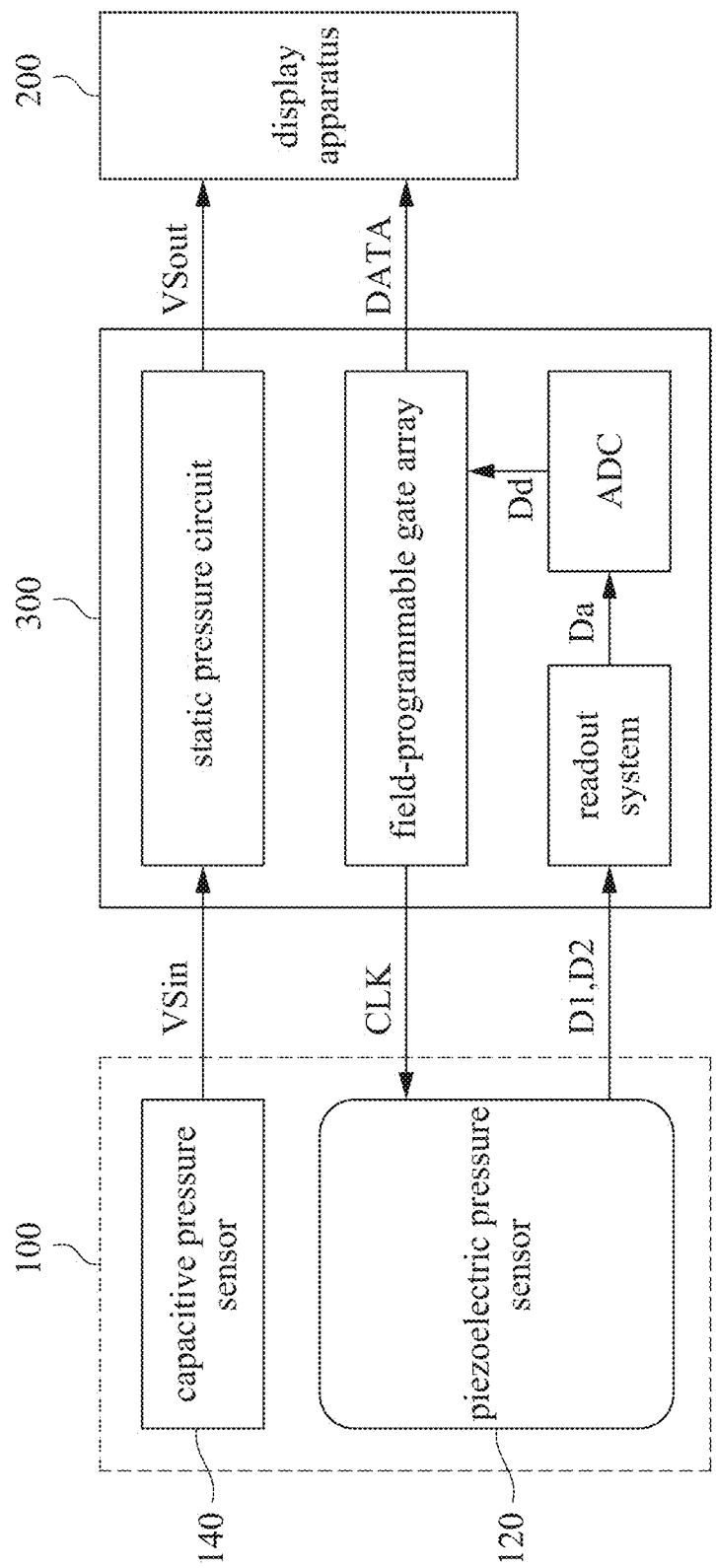
FIG. 2 is a schematic diagram illustrating a pulse measuring apparatus in accordance with some embodiments of the disclosure.

Please refer to FIG. 2. FIG. 2 is a schematic diagram illustrating a pulse measuring apparatus in accordance with some embodiments of the disclosure. As shown in FIG. 2, in some embodiments, the pulse measuring apparatus includes a sensing component 100, a display apparatus 200 and a processor 300. In some other embodiments, the pulse measuring apparatus further includes one or more indenters (not shown in figure). Configurationally, the processor 300 is electrically coupled to the sensing component 100, the display apparatus 200 and the indenters. Specifically, the processor 300 may be electrically coupled to the sensing component 100 through a flexible printed circuit (FPC), and electrically coupled to the display apparatus 200 through a data transmission line.

In practice, the processor 300 may be an integrated circuit such as a micro controller, a central processor, a microprocessor, a digital signal processor (DSP), an application specific integrated circuit (ASIC), a complex programmable logic device (CPLD) or logic circuit for arithmetic or data processing. In some embodiments, the display apparatus may be a human-machine interface, such as a computer, an oscilloscope, etc.

As shown in FIG. 2, the processor 300 includes a readout system, an analog-to-digital converter (ADC), a field-programmable gate array (FPGA), and a static pressure circuit. Configurationally, the piezoelectric pressure sensor 120 of the sensing component 100 is electrically coupled to the readout system and the field-programmable gate array. The analog-to-digital converter ADC is coupled to the readout system and the field-programmable gate array. The capacitive pressure sensor 140 of the sensing component 100 is electrically coupled to the static pressure circuit. The display apparatus 200 is electrically coupled to the field-programmable gate array and the static pressure circuit in the processor 300.

Operationally, the piezoelectric pressure sensor 120 is configured to receive a clock signal CLK from the field-programmable gate array in the processor 300, to measure the pulse at the corresponding position and to send the sensing signals D1, D2 to the readout system in the processor 300. The readout system amplitudes and/or converts the sensing signals D1, D2 into an analog data signal Da and sends the analog data signal Da to the analog-to-digital converter ADC. The analog-to-digital converter ADC converts the analog data signal Da into a digital data signal Dd and sends the digital data signal Dd to the field-programmable gate array. The field-programmable gate array performs calculations and data processing according to the received digital data signal Dd and outputs a display-data signal DATA to the display apparatus 200.

In some embodiments, the capacitive pressure sensor 140 in the sensing component 100 is configured to obtain a static pressure signal VSin, and send the amplified and/or regulated static pressure signal VSout to the display apparatus 200 through the static pressure circuit in the processor 300. The display apparatus 200 is configured to receive the display-data signal DATA of the processor 300 and amplified and/or regulated static pressure signal VSout to output and display. In addition, in some other embodiments, the processor 300 is configured to control the indenter to apply different forces to the wrist 900.

Figure 3A:
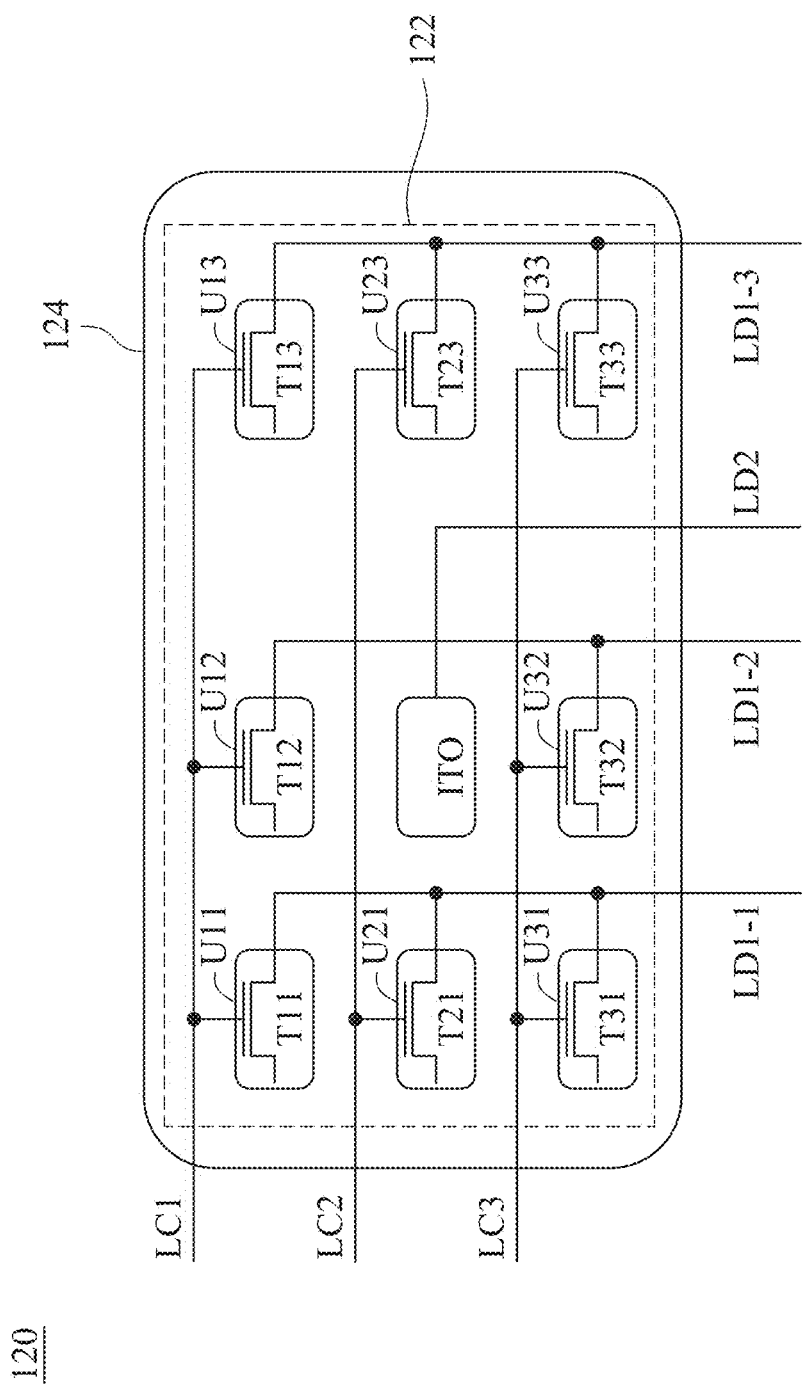
FIG. 3A is a schematic diagram illustrating a piezoelectric pressure sensor in accordance with some embodiments of the disclosure.

Please refer to FIG. 3A. FIG. 3A is a schematic diagram illustrating a piezoelectric pressure sensor 120 in accordance with some embodiments of the disclosure. As shown in FIG. 3A, the piezoelectric pressure sensor 120 includes a piezoelectric material layer 124, a thin film transistor array 122 and an induced electrode ITO. The thin film transistor array 122 includes eight detection elements U11~U33. As shown in figure, each one of the detection elements U11~U33 includes one of the transistors T11~T33 respectively. In some embodiment, the detection elements U11~U33 are arranged around an induced electrode ITO. In some other embodiments, the induced electrode ITO may be arranged to any position in the thin film transistor array 122. Furthermore, though there are eight detection elements U11~U33 and one induced electrode ITO illustrated in the FIG. 3A, the number is merely an example, not intended to limit the present disclosure. In other words, the number, the arranged direction and the arrangement distribution of the transistors and the induced electrode are merely examples, not intended to limit the present disclosure. Those of ordinary skills in the art without departing from the principle and spirit of the disclosure may adjust based on actual needs.

Figure 3B:
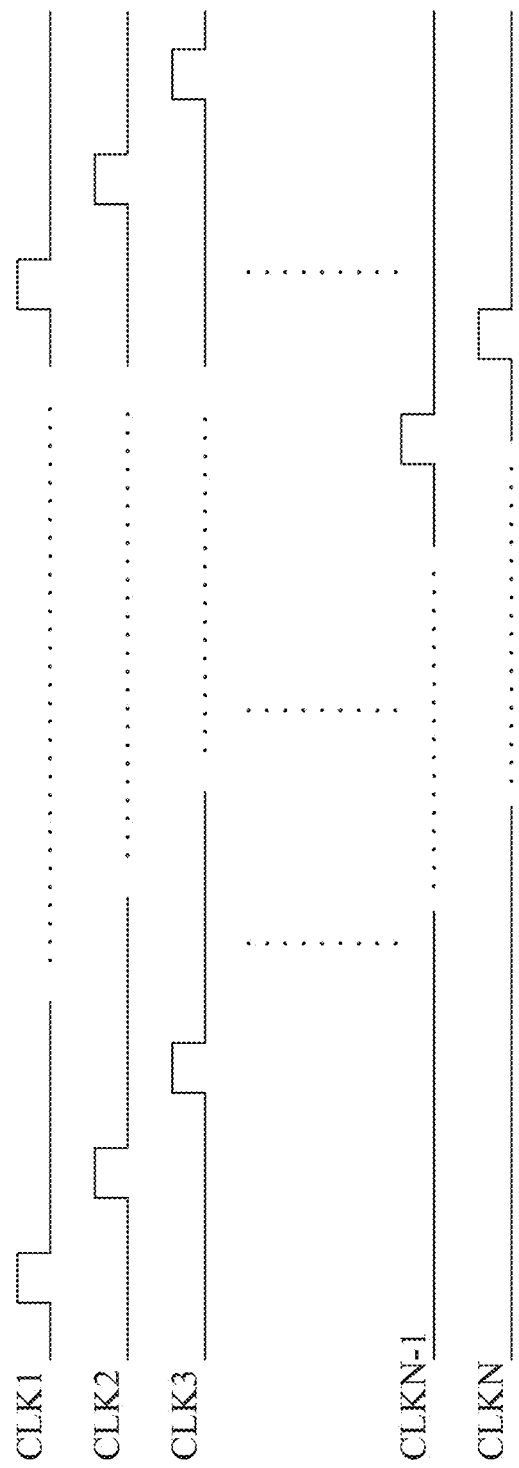
FIG. 3B is a schematic diagram illustrating clock signals in accordance with some embodiments of the disclosure.
Figure 3C:
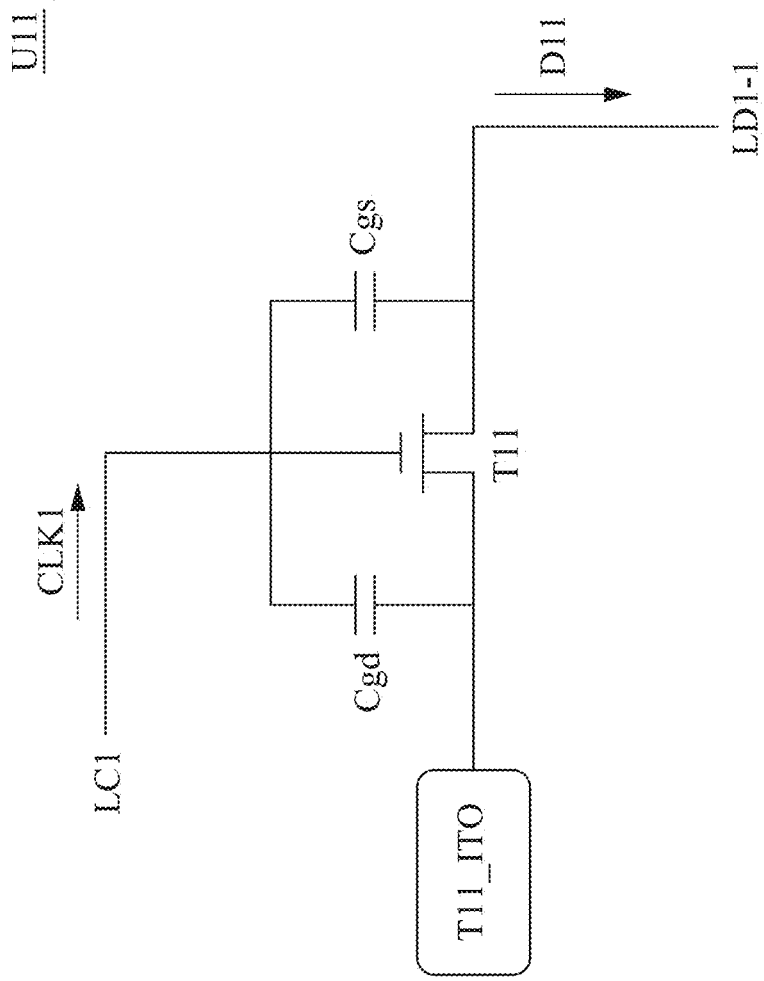
FIG. 3C is a schematic diagram illustrating a detection element in accordance with some embodiments of the disclosure.

Configurationally, the piezoelectric material layer 124 is covered on the thin film transistor array 122 and the induced electrode ITO, and the piezoelectric material layer 124 is coupled to the first terminal of the induced electrode ITO. The control terminals of the transistors T11, T12, T13 are coupled to the clock transmission line LC1, the control terminals of the transistors T21, T23 are coupled to the clock transmission line LC2, the control terminals of the transistors T31, T32, T33 are coupled to the clock transmission line LC3. The second terminals of the T11, T12, T13 are coupled to the data line LD1-1, the second terminals of the transistors T21, T23 are coupled to the data line LD1-2, the second terminals of the transistors T31, T32, T33 are coupled to the data line LD1-3. Please refer to FIG. 3C together; FIG. 3C is a schematic diagram illustrating a detection element U11 in accordance with some embodiments of the disclosure.

As shown in FIG. 3C, the detection element U11 includes a transistor T11 and an induced electrode T11_ITO. The first terminal of the transistors T11 is coupled to the second terminal of the induced electrode T11_ITO. The first terminal of the induced electrode T11_ITO is coupled to the piezoelectric material layer 124. The internal structure of the other detection elements U12~U33 in FIG. 3A are similar to the internal structure of the detection element U11 in FIG. 3C. In other words, each one of the detection elements U12~U33 in FIG. 3A includes one of the induced electrodes (not shown in FIG. 3A, may be referred to the induced electrode T11_ITO in FIG. 3C), the first terminals of the transistors T12-T33 are coupled to the piezoelectric material layer 124 through the induced electrodes of themselves respectively.

The second terminal of the induced electrode ITO is coupled to the data line LD2. In other words, the induced electrode ITO and any one of the transistors T11~T33 are not coupled to each other through the transmission lines LC1~LC3, LD1-1~LD1-3. In some embodiments, the induced electrode ITO and the transistors T11~T33 may be electrically coupled by the piezoelectric material layer. In addition, when the piezoelectric pressure sensor 120 includes multiple induced electrodes ITO, the multiple induced electrodes ITO are not coupled to each other through the transmission lines, the specific content will be described in following.

Operationally, the piezoelectric material layer 124 is configured to measure the pulse at multiple positions to generate the corresponding multiple pulse signals. The multiple first terminals of the transistors T11~T33 are configured to receive the multiple pulse signals generated from the piezoelectric material layer 124 respectively. The multiple second terminals of the transistors T11~T33 are configured to output multiple first sensing signals D1 according to the corresponding multiple pulse signals respectively. The multiple control terminals of the transistors T11~T33 are configured to receive multiple clock signals CLK (as shown in FIG. 3B) respectively. The induced electrode ITO is configured to receive the corresponding one of the pulse signals to output the second sensing signal D2.

As shown in FIG. 3C, configurationally, the first terminal of the transistor T11 is coupled to the induced electrode T11_ITO, and the induced electrode T11_ITO is coupled to the piezoelectric material layer 124. The control terminal of the transistor T11 is coupled to the clock transmission line LC1. The second terminal of the transistor T11 is coupled to the data line LD1-1. Operationally, the control terminal of the transistor T11 is configured to receive the clock signals CLK1 through the clock transmission line LC1. The first terminal of the transistor T11 is configured to receive the pulse signals generated by the piezoelectric material layer 124 through the induced electrode T11_ITO. The transistor T11 is configured to generate the sensing signal D11 according to the clock signals CLK1 and the pulse signals and to output the sensing signal D11 by the second terminal of the transistors T11 through the data line LD1-1.

It should be noted that, the coupling capacitor Cgd, Cgs are generated between the control terminal and the first terminal, the second terminal of the transistor T11. Because there is no clear discharge path in the coupling capacitor generated between the clock transmission line, the data line, and the like, in order to avoid inaccurate signals, it is necessary to wait for a complete discharge and then perform the next detection. Therefore, there will be an upper limit of the sampling frequency determined by the switching of the clock signals, and the read signals that are read may not fully reflect the maximum value or waveform of the actual signals. In other words, the switching frequency of the clock signals may be too slow due to the generation of the coupling capacitor. On the other hand, as the induced electrode ITO shown in FIG. 3A, because there is no switch and is not limited by the clock signal, the actual peak value of the pulse signals is able to be measured without distortion.

In some embodiments, for example, when the piezoelectric material layer 124 measures the pulse signals at the inch position of the wrist 900 (as the area A3 shown in FIG. 1A and FIG. 1B), the corresponding thin film transistor array 122 arranged on the inch position receives pulse signals measured by the piezoelectric material layer 124 to output multiple first sensing signals D1, and the induced electrode ITO arranged in the corresponding thin film transistor array 122 also receives the pulse signals measured by the piezoelectric material layer 124 to output the second sensing signal D2.

Further description, if the inch position is divided into nine squares, when the piezoelectric material layer 124 located at the upper left of nine squares measures the pulse signal, the first terminal of the transistor T11 in the thin film transistor array 122 in FIG. 3A receives the pulse signal. And the control terminal of the transistor T11 in the thin film transistor array 122 outputs the first sensing signal D1 through the second terminal of the transistor T11 according to the clock signal CLK. In addition, when the piezoelectric material layer 124 located at the center of nine squares measures the pulse signal, the first terminal of the induced electrode ITO receives the pulse signal so as to output the second sensing signal D2 through the second terminal of the induced electrode ITO.

In this way, by the different transistors in the thin film transistor array 122 or the induced electrode ITO arranged in the thin film transistor array 122, the pulses at multiple positions are be able to be measured, and the range of the pulse is able to be obtained. Furthermore, by the induced electrode ITO without switches, the real peak value of the pulse signals is able to be measured, and it is not affected by the frequency of the clock signal CLK or the signal distortion caused by the switch, etc.

Figure 4A:
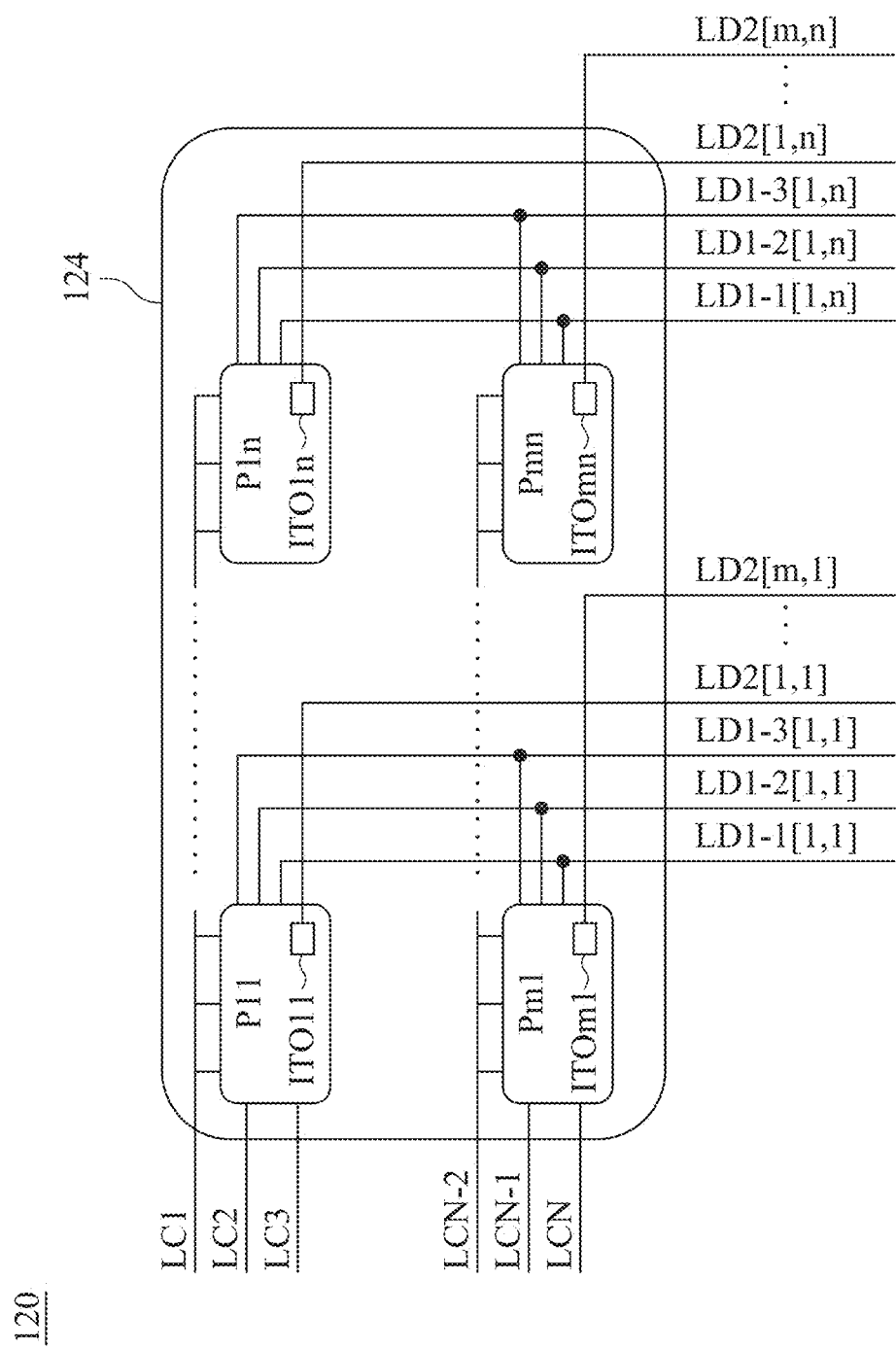
FIG. 4A is a schematic diagram illustrating a piezoelectric pressure sensor in accordance with some other embodiments of the disclosure.
Figure 4B:
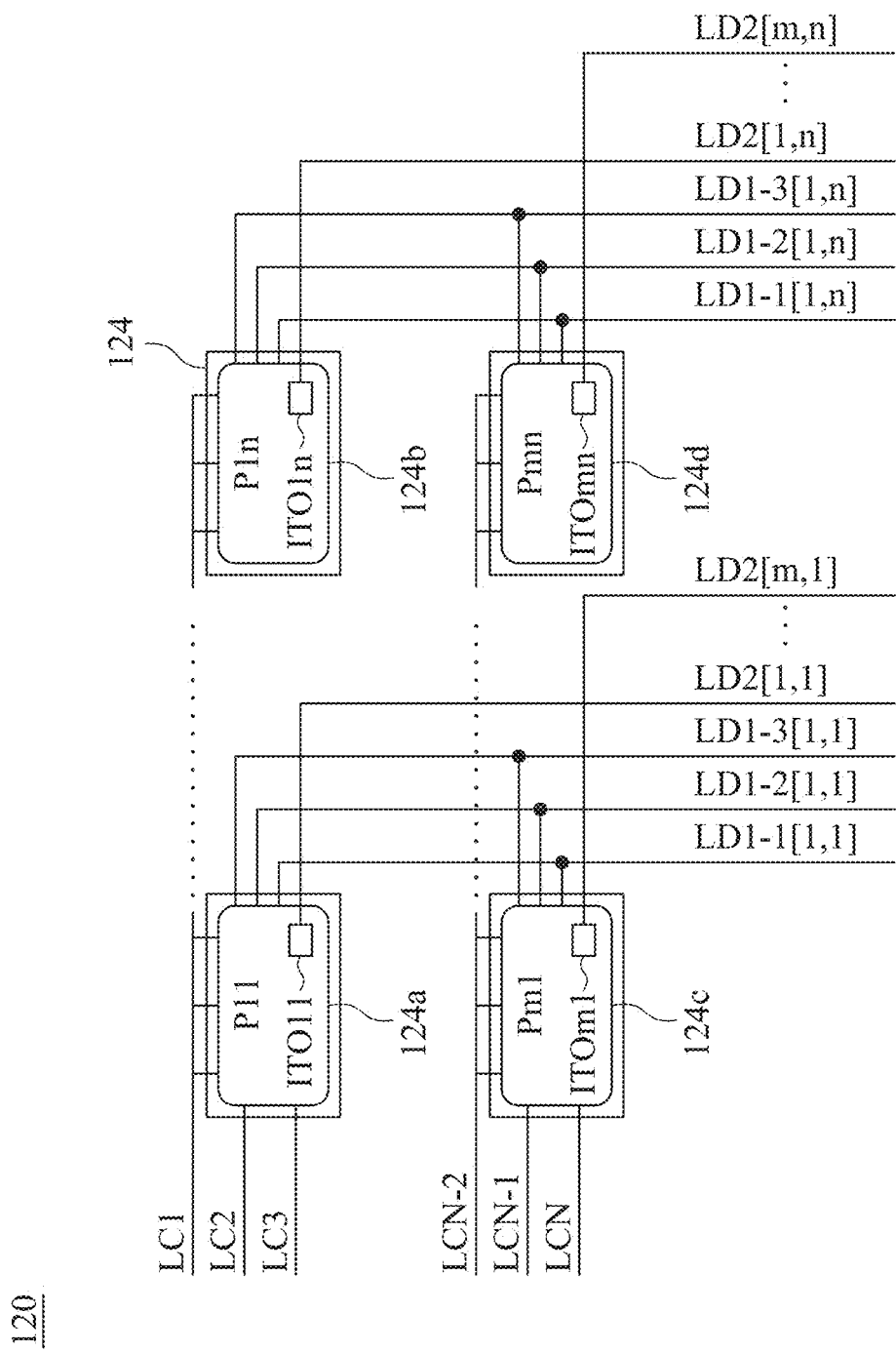
FIG. 4B is a schematic diagram illustrating another piezoelectric pressure sensor in accordance with some other embodiments of the disclosure.

Please refer to FIG. 4A. FIG. 4A is a schematic diagram illustrating a piezoelectric pressure sensor 120 in accordance with some other embodiments of the disclosure. As shown in FIG. 4A, the piezoelectric pressure sensor 120 includes the piezoelectric material layer 124 and the thin film transistor array P11~Pmn. Each thin film transistor array P11~Pmn includes eight transistors. One induced electrode ITO is arranged in the eight transistors. That is, every thin film transistor array P11~Pmn is arranged one of induced electrodes ITO11~ITOmn. However, the number is merely an example, not intended to limit the present disclosure. In addition, the piezoelectric material layer 124 in the present disclosure is not limited to a complete single layer piezoelectric material structure shown in FIG. 4A, in some other embodiments, the piezoelectric material layer 124 may be composed of multiple piezoelectric material blocks. As shown in FIG. 4B, the piezoelectric material layer of the piezoelectric pressure sensor 120 includes multiple piezoelectric material blocks 124a~124d. The piezoelectric material blocks 124a~124d are covered one or more thin film transistor arrays, so as to improve sensitivity. As the embodiments shown in FIG. 4B, the piezoelectric material block 124a is covered on the thin film transistor array P11, the piezoelectric material block 124b is covered on the thin film transistor array P1n, the piezoelectric material block 124c is covered on thin film transistor array Pm1, the piezoelectric material block 124d is covered on thin film transistor array Pmn. The total number of the piezoelectric material blocks in the piezoelectric material layer depends on the number of the actual thin film transistor array, not limited to the example shown in FIG. 4B. In some other embodiments, the thin film transistor array may include any integer number of the transistors. The thin film transistor array may also be arranged one or more induced electrodes ITO.

Configurationally, the piezoelectric material layer 124 is covered on the thin film transistor array P11~Pmn and multiple induced electrodes ITO11~ITOmn, and the piezoelectric material layer 124 is coupled to the first terminal of the transistors in the thin film transistor array P11~Pmn and the first terminals of the induced electrodes ITO11~ITOmn. The processor 300 is connected to the transistors of the first column to the Nth column through the clock transmission lines LC1~LCN respectively. That is, the transistors in the same column may be coupled to the processor 300 through the same clock transmission line to receive the clock signals. Similarly, the transistors in the first row to the 3n-th row are connected to the processor 300 through the data line LD1-1[1,1]~LD1-3[1,n] respectively. That is, the transistors in the same row may be coupled to the processor 300 through the same data line to output the first sensing signals D1.

In addition, the multiple induced electrodes ITO11~ITOmn arranged in the thin film transistor array P11~Pmn are connected to the processor 300 through the data line LD2[1,1]~LD2[m,n] respectively. That is, each induced electrode ITO11~ITOmn is singly coupled to one single data line LD2[1,1]~LD2[m,n] to output the second sensing signal D2 respectively.

Figure 5:
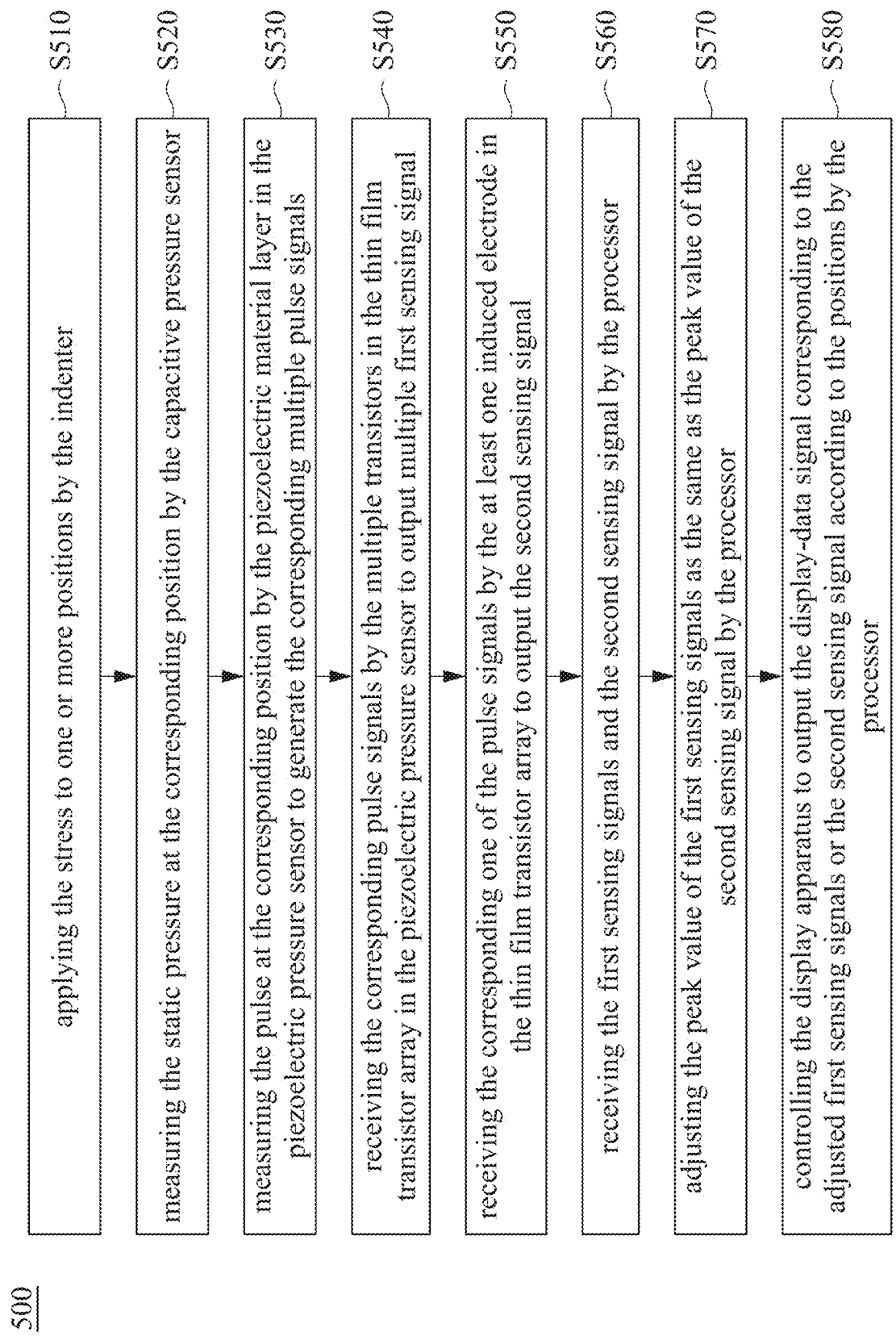
FIG. 5 is a flowchart illustrated a pulse measuring method in accordance with some embodiments of the disclosure.

Please refer to FIG. 5. FIG. 5 is a flowchart illustrated a pulse measuring method 500 in accordance with some embodiments of the disclosure. For the convenience and clarity of explanation, the pulse measuring method 500 following are described in accompany with embodiments of FIG. 1A-5, but not intended to limit it, various alterations and modifications may be performed on the disclosure by those of ordinary skills in the art without departing from the principle and spirit of the disclosure. As shown in FIG. 5, the pulse measuring method 500 includes operations S510~S580.

Firstly, in operation S510, applying the stress to one or more positions by the indenter. Specifically, one or more of the inch, bar and cubit positions of the wrist 900 are chosen, and the indenter is controlled by the processor 300 in the pulse measuring apparatus to apply the first stress, the second stress or the three stress to the corresponding position of the wrist 900, so as to simulate the different forces used by the Chinese medicine practitioner to diagnosis the pulse of floating, medium or sinking.

Next, in operation S520, measuring the static pressure at the corresponding position by the capacitive pressure sensor 140. Specifically, at the chosen position of the wrist 900, the capacitive pressure sensor 140 measures the first static pressure, the second static pressure or the third static pressure corresponding to the first stress, the second stress or the third stress respectively.

In addition, in some embodiments, the processor 300 receives the static pressure signal VSin of the first static pressure, the second static pressure and the third static pressure, so as to confirm that the force applied by the indenter is able to corresponding to different pulses of floating, medium or sinking. And the processor 300 controls the display apparatus 200 to display the amplitude of the static pressure signal VSout corresponding to the static pressure signal VSin.

Next, in operation S530, measuring the pulse at the corresponding position by the piezoelectric material layer 124 in the piezoelectric pressure sensor 120 to generate the corresponding multiple pulse signals. For example, when the indenter applies the first stress to the bar position of the wrist 900, the piezoelectric material layer 124 in the piezoelectric pressure sensor 120 measures the pulse at the corresponding position (as the area A2 shown in FIG. 1) to generate the corresponding multiple pulse signals.

Next, in operation S540, receiving the corresponding pulse signals by the multiple transistors T11~T33 in the thin film transistor array 122 in the piezoelectric pressure sensor 120 to output multiple first sensing signals D1. Specifically, the multiple first terminals of the multiple transistors T11~T33 receive the corresponding pulse signals respectively. And the multiple control terminals of the transistors T11~T33 output the multiple first sensing signals D1 through the multiple second terminal of the transistors T11~T33 according to the multiple clock signals CLK.

Next, in operation S550, receiving the corresponding one of the pulse signals by the at least one induced electrode ITO in the thin film transistor array 122 to output the second sensing signal D2. Specifically, the first terminal of the induced electrode ITO receives the corresponding pulse signals, and the second terminal of the induced electrode ITO outputs the second sensing signal D2.

Next, in operation S560, receiving the first sensing signals D1 and the second sensing signal D2 by the processor 300.

Next in operation S570, adjusting the peak value of the first sensing signals D1 as the same as the peak value of the second sensing signal D2 by the processor. Specifically, the transistors will mutate over time or the number of uses, so the amplitude of the first sensing signals D1 measured by different translators may not accurately reflect the magnitude of the pulse signals. Furthermore, because the transistor samples based on the switching frequency of the clock signals, there may be error due to the too slow switching frequency of the clock signals, and it is unsure that whether the first sensing signals D1 read may reflect the maximum value or waveform of the actual signal. And because the induced electrode ITO does not have a switch sensor, the amplitude of the second sensing signal D2 measured by the induced electrode ITO is able to accurately reflect the actual amplitude of the pulse signals. Accordingly, the processor adjusts the peak value of the first sensing signals D1 as the same as the peak value of the second sensing signal D2.

Next, in operation S580, controlling the display apparatus 200 to output the display-data signal DATA corresponding to the adjusted first sensing signals D1 or the second sensing signal D2 according to the positions by the processor 300.

Figure 6:
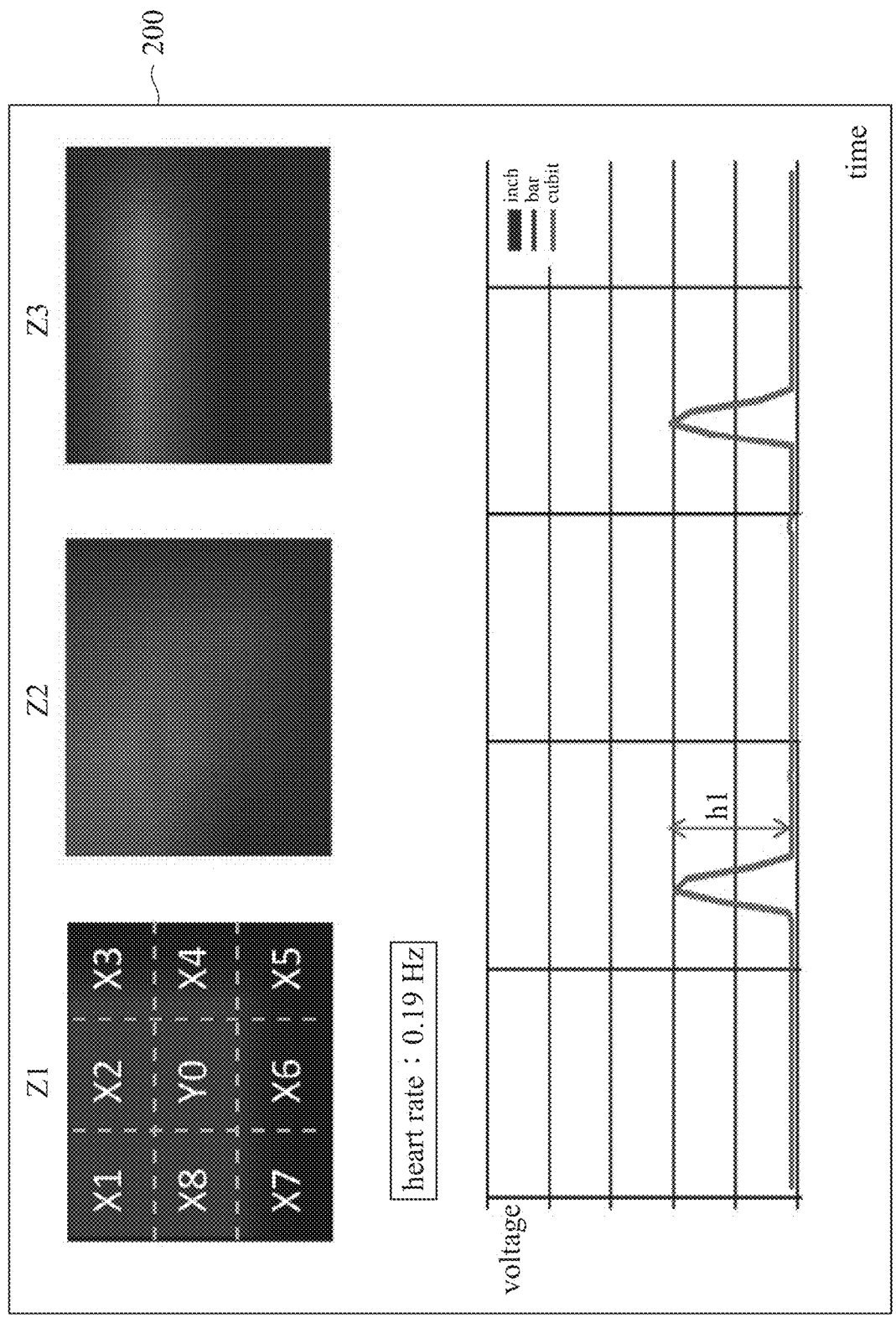
FIG. 6 is a schematic diagram illustrating a screen of a display apparatus in accordance with some other embodiments of the disclosure.

Please refer to FIG. 6. FIG. 6 is a schematic diagram illustrating a screen of a display apparatus 200 in accordance with some other embodiments of the disclosure. In some embodiments, the screen of the display apparatus 200 may include heart rate. As shown in FIG. 6 the heart rate is about 0.19 Hz. In some embodiments, the screen of the display apparatus 200 may include a dynamic waveform of the display-data signals DATA corresponding to the sensing signals D1 and D2. As shown in FIG. 6, the lower half of the screen of the display apparatus 200 is the dynamic waveform of the display-data signal DATA corresponding to the sensing signal D2, wherein the x-axis represents time, the Y-axis represents voltage, the amplitude h1 represents the strength of the pulse.

In addition, in some other embodiments, as shown in FIG. 6, the upper half of the screen of the display apparatus 200 may include the display blocks Z1, Z2 and Z3 representing the pulse of floating, medium and sinking respectively. Furthermore, the display block Z1 is taken as an example, the display block Z1 may be divided into multiple display areas X1~X8 and Y0 representing the distribution areas of the pulse at the corresponding position.

Specifically, the first sensing signals D1 measured by the thin film transistor array 122 corresponds to the first position (as the position at which the transistors T11~T33 located in FIG. 3), and the second sensing signal D2 measured by the induced electrode ITO corresponds to the second position (as the position at which the induced electrode ITO located in FIG. 3). The processor 300 is configured to control the display apparatus 200 to display the display-data signal DATA corresponding to one of the multiple first sensing signals D1 to one of the multiple display areas X1~X8 of the display apparatus 200 according to the first position. And the processor 300 is configured to control the display apparatus 200 to display the display-data signal DATA corresponding to the second sensing signal D2 to the display area Y0 of the display apparatus 200 according to the second position.

Furthermore, in some other embodiments, the processor 300 is configured to receive the first sensing signals D1 and the second sensing signal D2 and to adjust the peak value of the first sensing signals D1 as the same as the peak value of the second sensing signal D2. And the processor 300 is configured to control the display apparatus 200 to display the display-data signal DATA corresponding to the adjusted first sensing signals D1 or the second sensing signal D2 to the corresponding display areas X1~X8 or Y0.

In addition, when the indenter applies the first stress, the second stress or the third stress to the wrist 900, the processor 300 receives the static pressure signal VSin corresponding to the first static pressure, the second static pressure or the third static pressure from the capacitive pressure sensor 140 respectively, and the processor 300 receives the first set of sensing signals, the second set of sensing signals or the third set of sensing signals. The processor 300 controls the display apparatus 200 to output the display data signal DATA corresponding to the first sensing signals to display according to the static pressure signal VSin corresponding to the first static pressure, the second static pressure or the third static pressure. In other words, the processor 300 control the display apparatus 200 to display the display-data signals DATA corresponding to the first set of sensing signals, the second set of sensing signals or the third set of sensing signals to the display blocks Z1, Z2 or Z3 respectively. In some other embodiments, the processor 300 is configured to determine the amplitude of the first set of sensing signals, the second set of sensing signals or the third set of sensing signals, so as to display the largest one of the display-data signal DATA corresponding to the first set of sensing signals, the second set of sensing signals or the third set of sensing signals.

It should be noted that the distribution of the display screen, the number of display areas, the division method or the area size described above are merely examples for convenience of explanation, not intended to limit the present disclosure. Those of ordinary skills in the art without departing from the principle and spirit of the disclosure may adjust based on actual needs.

In this way, by the operations S510-S580 above, the pulse at one of the cubit, bar or inch positions of the left or right hands is able to be measured, and the three waveforms corresponding to the floating, medium or sinking force are able to be obtained. In some embodiments, the operations S510-S580 of the pulse measuring method 500 may be cyclically executed to measure the pulse at another one of the cubit, bar or inch positions of the left or right hands. In some other embodiments, the pulse at two or all of the cubit, bar or inch positions may be measured by the pulse measuring method 500.

How to perform operations and functions of the pulse measuring method 500 based on the various pulse measuring apparatus in the different embodiments above is able to be directly understood by those of ordinary skilled in the art, so it is omitted for the sake of brevity and not repeated herein.

In summary, in the pulse measuring apparatus and the pulse measuring method of the present disclosure, the pulse rate and strength reflected at the cubit, bar, inch positions of the left and right hands with the floating, medium, sinking force are be able to be obtained, so that the health of different organs is able to be inferred. The pulse signals are measured by the induced electrode to output a second sensing signal, and the peak values of the first sensing signals measured by the thin film transistor array is corrected, so that the accuracy of the pulse measurement result is improved, and thus the pulse measurement method is improved.

Although specific embodiments of the disclosure have been disclosed with reference to the above embodiments, these embodiments are not intended to limit the disclosure. Various alterations and modifications may be performed on the disclosure by those of ordinary skills in the art without departing from the principle and spirit of the disclosure. Thus, the protective scope of the disclosure shall be defined by the appended claims.

What is claimed is:

1. A sensing component, comprising: a piezoelectric pressure sensor, comprising: a piezoelectric material layer, configured to measure pulses at a plurality of positions to generate a plurality of corresponding pulse signals; a thin film transistor array, coupled to the piezoelectric material layer, wherein the thin film transistor array comprises a plurality of transistors, one of the transistors comprises: a first terminal, configured to receive one of the plurality of pulse signals; a second terminal, coupled to a data line, configured to output a first sensing signal according to the one of the plurality of pulse signals; a control terminal, configured to receive a clock signal; and an induced electrode, coupled to the piezoelectric material layer, configured to receive another one of the plurality of pulse signals to output a second sensing signal; and wherein the sensing component further comprises: a processor, coupled to the sensing component, configured to receive a plurality of first sensing signals and the second sensing signal, and to adjust the peak values of the plurality of first sensing signals as the same as the peak value of the second sensing signal, and to control a display apparatus to display a corresponding display-data signal according to the plurality of first sensing signals adjusted.

2. The sensing component of claim 1, wherein the induced electrode and any one of the plurality of transistors are not coupled to each other.

3. The sensing component of claim 1, wherein the plurality of transistors are arranged around the induced electrode.

4. The sensing component of claim 1, wherein the sensing component further comprises:
a capacitive pressure sensor, coupled to the piezoelectric pressure sensor, when a pulse measuring apparatus applies a stress to the plurality of positions, the capacitive pressure sensor configured to measure a static pressure value of the plurality of positions.

5. The sensing component of claim 1, wherein the first sensing signal is corresponding to a first position of the plurality of positions, the processor is configured to control the display apparatus according to the first position, so as to make the display apparatus display the corresponding display-data signal to one of a plurality of display areas according to the first sensing signal adjusted.

6. The sensing component of claim 1, wherein the sensing component further comprises: a capacitive pressure sensor, coupled to the piezoelectric pressure sensor, wherein when a pulse measuring apparatus applies a first stress, a second stress or a third stress to the plurality of positions respectively, the capacitive pressure sensor measures a first static pressure, a second static pressure or a third static pressure of the plurality of positions respectively, the piezoelectric pressure sensor measures a first set of sensing signals, a second set of sensing signals or a third of sensing signals, the processor controls the display apparatus to display corresponding one of the first set of sensing signals, the second set of sensing signals and the third of sensing signals according to the first static pressure, the second static pressure or the third static pressure.

7. A pulse measuring method, comprising: measuring, by a piezoelectric material layer of a piezoelectric pressure sensor, pulses of a plurality of positions to generate a corresponding plurality of pulse signals; receiving, by a plurality of transistors in a thin film transistor array in the piezoelectric pressure sensor, the corresponding plurality of pulse signals to output a plurality of first sensing signals; receiving, by at least an induced electrode in the piezoelectric pressure sensor, one of the plurality of pulse signals to output a second sensing signal; and further comprising: receiving, by a processor, the plurality of first sensing signals and the second sensing signal; adjusting, by the processor, the peak values of the plurality of first sensing signals as the same as the peak value of the second sensing signal; and controlling, by the processor, a display apparatus to display a display-data signal corresponding to the adjusted the plurality of first sensing signals or the second sensing signal according to the plurality of positions.

8. The pulse measuring method of claim 7, further comprising:
applying, by a indenter, a stress to the plurality of positions; and
measuring, by a capacitive pressure sensor, a static pressure of the plurality of positions.

* * * * *